United States Patent [19]

Sensui et al.

[11] Patent Number: 4,597,795
[45] Date of Patent: Jul. 1, 1986

[54] 6-TETRAHYDROFURFURYLAMINOFLUORAN COMPOUND USEFUL AS A COLOR FORMER

[75] Inventors: Hideyuki Sensui, Tokyo; Susumu Suzuka, Yono; Michihiro Gonda, Kitamoto; Katsumasa Kikkawa, Tokyo, all of Japan

[73] Assignee: Hodogaya Chemical Co., Ltd., Tokyo, Japan

[21] Appl. No.: 693,116

[22] Filed: Jan. 22, 1985

[30] Foreign Application Priority Data

Mar. 5, 1984 [JP] Japan ................... 59-40526
Apr. 3, 1984 [JP] Japan ................... 59-65097

[51] Int. Cl.[4] ............................... C07D 493/10
[52] U.S. Cl. ...................... 106/21; 346/221; 549/226
[58] Field of Search ............ 549/226; 106/21; 346/221

[56] References Cited

U.S. PATENT DOCUMENTS 3,681,390  8/1972  Lin ........................ 549/226 X

FOREIGN PATENT DOCUMENTS

| 43-4160 | 2/1968 | Japan . |
| 44-3680 | 2/1969 | Japan . |
| 49-17748 | 5/1974 | Japan . |
| 51-23204 | 7/1976 | Japan . |
| 51-29180 | 8/1976 | Japan . |
| 2002801A | 2/1979 | United Kingdom . |
| 2105737A | 3/1983 | United Kingdom . |

Primary Examiner—Richard L. Raymond
Attorney, Agent, or Firm—McAulay, Fields, Fisher, Goldstein & Nissen

[57] ABSTRACT

A novel 6-tetrahydrofurfurylaminofluoran compound useful as a color former (precursory colorant) for a heat-sensitive recording sheet is of the formula (I):

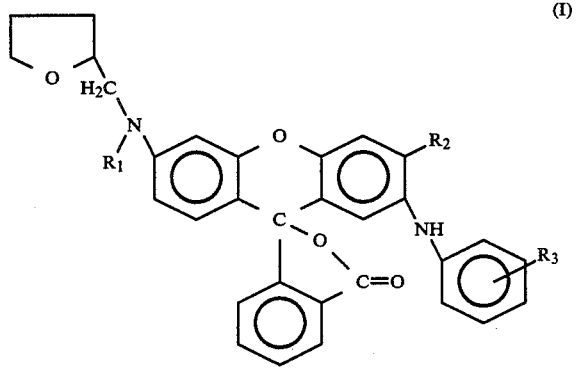

wherein $R_1$ is H, $C_{1-8}$ alkyl, tetrahydrofurfuryl, phenyl, alkyl($C_{1-5}$)phenyl, or $C_{3-8}$ cyclic alkyl, $R_2$ is H, Cl, F, $C_{1-5}$ alkyl, $C_{1-5}$ alkoxy, $C_{2-10}$ alkoxyalkyl, phenyl or benzyl, and $R_3$ is H, Cl, F, $C_{1-5}$ alkyl and $C_{2-7}$ acryl.

3 Claims, No Drawings

6-TETRAHYDROFURFURYLAMINOFLUORAN COMPOUND USEFUL AS A COLOR FORMER

BACKGROUND OF THE INVENTION

1. Field of the Invention

The present invention relates to a novel 6-tetrahydrofurfurylaminofluoran compound. More particularly, the present invention relates to a novel 6-tetrahydrofurfurylaminofluoran compound useful as a color former for heat sensitive recording sheets, pressure-sensitive recording sheets or electrical heat-sensitive recording sheets being capable of forming clear color images thereon and having a satisfactory fastness against humidity and oily substances.

2. Description of the Related Art

Certain type of heat-sensitive recording sheets which comprises a recording layer containing a color-former (precursory colorant) and coated on a substrate sheet, for instance, paper, are disclosed by Japanese Examined Patent Publication (Kokoku) Nos. 43-4160, 44-3680 and 49-17748.

When the recording layer is heated imagewise with a heating head in a thermal printer, the color former produces color images on the recording layer. The color is usually black.

The heat-sensitive recording sheets are advantageous in that they are low cost and in that the recording operation can be carried out quietly at a high recording speed. Thus, the heat-sensitive recording sheets are useful for a facsimile printer.

Color-forming fluoran compounds are disclosed in U.S. Pat. No. 3,681,390, which discloses a color former consisting of 2-anilino-3-methyl-6-diethylaminofluoran; Japanese Examined Patent Publication (Kokoku) No. 51-23204, which discloses 2-anilino-3-methyl-6-N-methyl-N-cyclohexylaminofluoran usable as a color former; Japanese Examined Patent Publication (Kokoku) No. 51-29180, which discloses 2-anilino-3-methyl-6-N-ethyl-N-(p-methylphenyl)aminofluoran usable as a color former; and U.K. Patent Application GB No. 2002801A, which discloses 2-anilino-3-methyl-6-N-ethyl-N-isoamylaminofluoran usable as a color former. In addition, U.K. Patent Application No. GB 2105737A discloses 2-anilino-3-chloro-6-aminofluoran compounds usable as color formers.

The above-mentioned conventional color-forming fluoran compounds are disadvantageous in that the color-initiating temperature thereof necessary for forming color images with a satisfactory color density (depth) of 1.0 or more is unsatisfactorily high, and therefore, the energy consumption necessary for forming color images having a satisfactory color density is disadvantageously large, and in that the color fastness of the resultant color images against light, heat, humidity, and oily substances is unsatisfactory.

Also, the color former contained in the heat sensitive recording sheets should not form color at a lower temperature and under a lower pressure than those to be applied to the recording sheet when the color images are to be formed. The known color formers are not always satisfactory in the above-mentioned properties.

Accordingly, it is highly desirable to provide a compound usable as a color former for heat-sensitive, pressure-sensitive, or electrical heat-sensitive recording sheets and free from the above-mentioned disadvantages.

SUMMARY OF THE INVENTION

An object of the present invention is to provide a novel 6-tetrahydrofurfurylaminofluoran compound useful as an electron donative color former (precursory colorant) for heat sensitive recording sheets, which compound has an excellent heat sensitivity for color-forming.

Another object of the present invention is to provide a novel 6-tetrahydrofurfurylaminofluoran compound useful as a color former capable of forming deep black color images having a superior color fastness against humidity and oily substances.

The above-mentioned objects can be attained by the 6-tetrahydrofurfurylaminofluoran compound of the present invention having the formula (I):

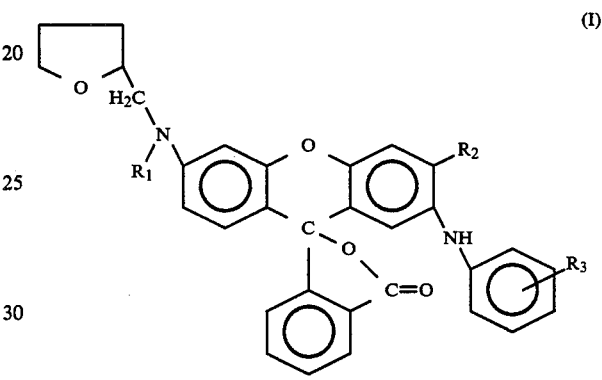

wherein $R_1$ represents a member selected from the group consisting of a hydrogen atom, alkyl radicals having 1 to 8 carbon atoms, a tetrahydrofurfuryl radical, a phenyl radical, an alkylphenyl radical in which the alkyl group has 1 to 5 carbon atoms, and cyclic alkyl radicals having 3 to 8 carbon atoms; $R_2$ represents a member selected from the group consisting of a hydrogen atom, chlorine atom, fluorine atom, alkyl radicals having 1 to 5 carbon atoms, alkoxy radicals having 1 to 5 carbon atoms, alkoxyalkyl radicals having 2 to 10 carbon atoms, a phenyl radical, and a benzyl radical; and $R_3$ represents a hydrogen atom, chlorine atom, fluorine atom, alkyl radicals having 1 to 5 carbon atoms and acyl radicals having 2 to 7 carbon atoms.

The 6-tetrahydrofurfury laminofluoran compound of the present invention is useful as a principal component of a heat sensitive color former. The color former is preferably contained in a heat sensitive recording layer of a heat sensitive recording sheet.

DESCRIPTION OF THE PREFERRED EMBODIMENTS

The 6-tetrahydrofurfurylaminofluoran compound of the present invention is stable in air and is a colorless or substantially colorless solid substance. The compound produces a black color when brought into contact with an acidic (electron acceptor) material, for example, a phenol derivative such as bisphenol A or a p-hydroxybenzoic acid derivative such as benzyl p-hydroxybenzoic ester at an elevated temperature.

The 6-tetrahydrofurfurylaminofluoran compound of the present invention can be prepared by the following process. In the process, a diphenylamine derivative of formula (II):

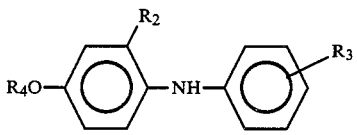

wherein $R_2$ and $R_3$ are as defined above and $R_4$ represents a member selected from the group consisting of a hydrogen atom, an acetyl radical, and alkyl radicals having 1 to 5 carbon atoms, is brought into reaction with a benzophenone derivative of formula (III):

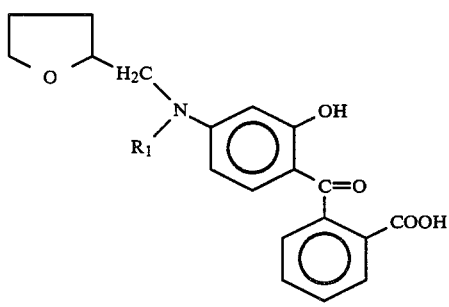

wherein $R_1$ is as defined above, in the presence of a condensing agent consisting of, for example, sulfuric acid having a concentration of 80% to 100% at a temperature of from 0° C. to 80° C. for a necessary time period, for example, 1 to 10 hours. The resultant reaction mixture is mixed with water, and the pH of the mixture is adjusted to 8 to 10 by adding sodium hydroxide, to allow a precipitate to be produced from the mixture. The precipitate is separated from the mixture by means of filtration. The resultant cake is mixed with toluene and with a 5 to 10% sodium hydroxide aqueous solution. The mixture is stirred at a temperature of 90° C. for 1 to 3 hours while refluxing, to separate a toluene phase from the mixture. The separated toluene phase is removed from the mixture, washed with water, and concentrated to separate a deposit from the toluene phase. The crystalline deposit is removed from the toluene phase and is dried. The resultant crystalline deposit consists of the 6-tetrahydrofurfurylaminofluoran compound of formula (I) which is substantially colorless.

The above-mentioned process is effective for producing the compound of formula (I) having a high purity in a high yield. If necessary, the crystalline deposit may be recrystallized from a volatile organic solvent consisting of toluene, acetone, butyl acetate, or cyclo hexane.

In the above-mentioned process, the sulfuric acid having a concentration of from 80% to 100% is preferably used as a condensing agent and as a solvent for the benzophenone derivative of formula (III). The condensing agent may be selected from concentrated sulfuric acid, acetic anhydride, phosphoric acid, polyphosphoric acid, phosphorus oxychlonate, and zinc chloride.

The 6-tetrahydrofurfurylaminofluoran compound of formula (I) can be selected from 2-anilino-3-methyl-6-N-methyl-N-tetrahydrofurfurylaminofluoran, 2-anilino-3-methyl-N-ethyl-N-tetrahydrofurfurylaminofluoran, 2-anilino-3-chloro-6-N-methyl-N-tetrahydrofurfurylaminofluoran, 2-(2-chloroanilino)-6-N-methyl-N-tetrahydrofurfurylaminofluoran, 2-(2-chloroanilino)-6-N,N-ditetrahydrofurfurylaminofluoran, 2-anilino-3-methyl-6-N,N-ditetrahydrofurfurylaminofluoran, 2-anilino-3-methyl-6-N-isoamyl-N-tetrahydrofurfurylaminofluoran, 2-anilino-3-methyl-6-N-butyl-N-tetrahydrofurfurylaminofluoran, 2-anilino-3-ethoxyethyl-6-N-methyl-N-tetrahydrofurfurylaminofluoran, 2-anilino-3-methyl-N-p-tolyl-N-tetrahydrofurfurylaminofluoran, 2-anilino-3-methyl-6-N-cyclohexyl-N-tetrahydrofurfurylaminofluoran, 2-anilino-3-methyl-N-tetrahydrofurfurylaminofluoran, 2-anilino-3-phenyl-6-N-methyl-N-tetrahydrofurfurylaminofluoran, 2-anilino-3-phenyl-6-N-ethyl-N-tetrahydrofurfurylaminofluoran, 2-anilino-3-benzyl-6-N-methyl-N-tetrahydrofurfurylaminofluoran, 2-anilino-3-methoxy-6-N-methyl-N-tetrahydrofurfurylaminofluoran, 2-p-toluidino-3-methyl-6-N-methyl-N-tetrahydrofurfurylaminofluoran, 2-(p-benzoyl-phenylamino)-3-ethyl-6-N-methyl-N-tetrahydrofurfurylaminofluoran, 2-(2-fluoroanilino)-6-N-methyl-N-tetrahydrofurfurylaminofluoran, and 2-anilino-3-benzyl-6-N,N-ditetrahydrofurfurylaminofluoran.

The 6-tetrahydrofurfurylaminofluoran compound of the invention produces a black color when it is brought into contact at an elevated temperature with an acidic substance, for example, silica gel or a phenolic compound.

When some of the 6-tetrahydrofurfurylaminofluoran compounds of formula (I) are developed on a thin layer of silica gel, the hues produced are shown in Table 1.

TABLE 1

| Item No. | Substituent $R_1$ | $R_2$ | $R_3$ | Hue |
|---|---|---|---|---|
| 1 | —$CH_2CH_3$ | —$CH_3$ | H | Black |
| 2 | —$CH_3$ | —$CH_3$ | H | Black |
| 3 | —$CH_2$—(tetrahydrofuryl) | —$CH_3$ | H | Black |
| 4 | —$CH_3$ | H | 2-Cl | Black |
| 5 | —$CH_3$ | —Cl | H | Greenish Black |
| 6 | —$CH_2$—(tetrahydrofuryl) | —H | 2-Cl | Black |
| 7 | —$CH_2CH_2CH(CH_3)_2$ | —$CH_3$ | H | Black |
| 8 | —$C_4H_9(n)$ | —$CH_3$ | H | Black |
| 9 | —$CH_3$ | —$C_2H_4OC_2H_5$ | H | Black |
| 10 | —$C_6H_4$—$CH_3$ | —$CH_3$ | H | Black |
| 11 | —$C_6H_5$ | —$CH_3$ | H | black |
| 12 | H | $CH_3$ | H | Reddish Black |
| 13 | —$CH_3$ | —$C_6H_5$ | H | Black |
| 14 | —$C_2H_5$ | —$C_6H_5$ | H | Black |

TABLE 1-continued

| Item No. | R₁ | R₂ | R₃ | Hue |
|---|---|---|---|---|
| 15 | —CH₃ | —CH₂— | H | Black |
| 16 | —CH₃ | —OCH₃ | H | Black |
| 17 | —CH₃ | —CH₃ | 4-CH₃ | Black |
| 18 | —CH₃ | —CH₂CH₃ —CO— | | Black |
| 19 | —CH₃ | H | 2-F | Black |
| 20 | —CH₂— | —CH₂— | H | Black |
| 21 | —CH₃ | H | —COCH₃ | Black |
| 22 | —C₂H₅ | H | —COCH₃ | Black |

A heat-sensitive color former consisting of at least one 6-tetrahydrofurfurylaminofluoran compound of the present invention is useful for a heat sensitive recording sheet.

In the recording sheet, a heat sensitive recording layer is formed on a substrate sheet, for example, paper, plastic sheet, or resin-coated paper. The heat sensitive recording layer comprises a color former consisting of at least one 6-tetrahydrofurfurylaminofluoran compound of formula (I), a color developing agent, and a resinous bonding agent.

The color former is used in an amount of 3 to 20% based on the dry weight of the recording layer.

The color-developing agent consists of at least one member selected from, for example, 4-t-butylphenol, 4-phenylphenol, methyl 4-hydroxybenzoate, 4,4'-isopropylidene diphenol, 4,4'-isopropylidene bis(2,6-dibromophenol), bis(4-hydroxyphenyl)sulfon, benzyl p-hydroxybenzoate, sec-butyl p-hydroxybenzoate, and 3-(α-methylbenzyl)salicylate, and is used in an amount of 5% to 45% based on the dry weight of the recording layer.

The resinous bonding agent consists of at least one water-soluble or water-insoluble resinous material selected from, for example, polyvinyl alcohol, methyl cellulose, hydroxyethyl cellulose, carboxymethyl cellulose, gum arabic, starch, gelatin, casein, polyvinyl pyrrolidone, and styrene-maleic anhydride copolymers. A preferable resinous bonding agent is a water-soluble bonding agent consisting of polyvinyl alcohol.

The recording layer optionally comprises an additive, for example, a filler consisting of, for example, aluminum hydroxide, calcium carbonate, magnesia, barium sulfate or calcium stearate, and/or a sensitizing agent consisting of, for instance, dimethyl terephthalate, dibenzyl terephthalate, β-naphthol benzyl ether, stearic amide, and/or benzyl p-benzyloxybenzoate. The filler and sensitizing agent are effective for making the resultant color images dark and clear. The filler and the sensitizing agent are used in an amount of 50% or less and 40% or less, based on the dry weight of the recording layer, respectively.

The recording layer optionally contains at least one heat-fusible substance, for example, stearic amide, oleic amide, ethylene bisstearoamide, benzene sulfoanilide, or benzyloxyacetanilide, when the fluoran compound and the color developing agent are not heat fusible at a temperature at which the recording procedures are applied to the recording sheet.

In the preparation of the recording sheet, a coating liquid is prepared from a color former consisting of at least one 6-tetrahydrofurfurylaminofluoran compound of the present invention, a color developing agent, a resinous bonding agent, and optionally, a filler, a sensitizing agent and a liquid medium.

Preferably, the color former and the color-developing agent will not dissolve in the liquid medium. Therefore, the liquid medium preferably consists of water and otherwise, at least one hydrocarbons, for example, cyclohexane or ligroin.

The coating liquid preferably comprises 1 part by weight of the color former, 2 to 10 parts by weight of the color developing agent, 0 to 10% by weight of the heat-fusible substance, 2 to 10 parts by weight of a resinous binding agent, and 5 to 150 parts by weight of a liquid medium.

The coating liquid may additionally contain at least one further additive, for example, a dispersing agent consisting of at least one member selected from, for example, sodium dioctylsulfosuccinate and sodium dodecylbenzene sulfonate, a ultraviolet ray-absorber which may consist of a benzophenon type or triazol type compound, a deforming agent, a fluorescent brightening agent, and a coloring material.

The coating liquid is applied to a surface of a substrate sheet by a known coating method and the coating liquid layer is solidified by evaporating the liquid medium.

The resultant recording layer is preferably in an amount of 2 to 15 g/m², more preferably from 3 to 10 g/m².

SPECIFIC EXAMPLES

The present invention will be further illustrated by the following examples which are representative and do not restrict the scope of the present invention in any way.

In the examples, the color-forming sensitivity of a recording layer containing a color former was represented by $T_{1.0}$ which refers to a temperature at which the color former produces a color image having a color density of 1.0. The measurement of the $T_{1.0}$ was carried out by using a Rhodiaceta type thermotester designed by the French National Textile Institute, at a temperature of from 60° C. to 170° C. under a pressure of 100 g/cm² for 3 seconds. The lower the $T_{1.0}$, the higher the heat-sensitivity of the recording layer.

Also, the color fastness of the resultant color images against humidity was determined in such a manner that the color images having a color density of 1.0 on a recording layer were exposed to an air atmosphere at a temperature of 50° C. and relative humidity of 90% for 24 hours. Thereafter, the color density ($D_1$) of the exposed color images was measured by using a Macbeth RD-514 type reflection color density tester.

The color fastness against humidity was calculated in accordance with the following equation:

$$\text{Humidity color fastness (\%)} = (D_1/1.0) \times 100$$

The color fastness of the color images against oily substances was determined in the following manner. That is, a solution containing 5% by weight of caster oil in chloroform was coated on a polyester film by means of a film applicator (20μ scale), and the layer of caster oil solution was air-dried. Color images having a color density of 1.0 and formed on a recording layer were coated with the air-dried caster oil on the polyester film by using a rubber stamp having a length of 1.5 cm and a width of 1 cm. The recording layer having the coated color images was placed in a constant temperature constant humidity container at a temperature of 50° C. and a relative humidity of 90% for a 3 hours. The resultant color density ($D_2$) of the color image was determined. The color fastness of the color images against oily substances is determined in accordance with the following equation:

Color fastness against oily substance
(%)=($D_2$/1.0)×100

EXAMPLE 1

Preparation of
2-anilio-3-methyl-6-N-ethyl-N-tetrahydrofurfurylaminofluoran

A solution was prepared by mixing 16.6 g of 2-(4-N-ethyl-N-tetrahydrofurfurylamino-2-hydroxy-benzoyl)-benzoic acid to 150 g of a 98% sulfuric acid and maintaining the mixture at a temperature of approximately 5° C. until the compound was completely dissolved in the sulfuric acid. The solution was mixed with 11.5 g of 2-methyl-4-methoxydiphenylamine and the reaction mixture was maintained at a temperature of 5° C. to 10° C. for 10 hours, and then at a temperature of 20° C. to 25° C. for 6 hours. The resultant reaction mixture was added to 1 l of iced later and the pH or the mixture was adjusted to 10 or more by adding sodium hydroxide. The resultant precipitate was collected from the mixture by means of filtration, the collected cake of precipitate was mixed with 450 ml of toluene and with 340 g of a 10% sodium hydroxide aqueous solution, and the resultant mixture was stirred at a temperature of 90° C. for 2 hours while refluxing. The toluene phase was collected from the mixture and subjected to a steam distillation to remove the toluene. The resultant crystalline deposit was collected by means of filtration, washed with 50 ml of methyl alcohol, recrystallized from toluene, and collected by means of filtration. The resultant crystals were then dried. The dried crystals consisted of 17.8 g of 2-anilino-3-methyl-6-N-ethyl-N-tetrahydrofurfurylaminofluoran having a melting point of from 165° C. to 167° C.

The solution of the resultant compound in a 95% acetic acid aqueous solution exhibited a first molecular extinction coefficient of $1.944 \times 10^4$ at a λ max of 452 nm and a second molecular extinction coefficient of $1.949 \times 10^4$ at a λ max of 594 nm.

A solution of the resultant compound was colorless and rapidly produced a black color when placed in contact with silica gel.

EXAMPLE 2

Preparation of
2-anilino-3-methyl-6-N-methyl-N-tetrahydrofurfurylaminofluoran 2-(4-N-methyl-N-tetrahydrofurfurylamino-2-hydroxybenzoyl)-benzoic acid in an amount of 16.0 g was completely dissolved in 150 g of a 95% sulfuric acid at a temperature of approximately 5° C. The solution was mixed with 11.5 g of 2-methyl-4-methoxydiphenylamine. The mixture was maintained at a temperature of 5° to 10° C. for 10 hours.

The resultant reaction mixture was treated in the same manner as that described in Example 1, and the resultant crystalline deposit was recrystallized from ethyl alcohol. White crystals consisting of 2-anilino-3-methyl-6-N-methyl-N-tetrahydrofurfurylaminofluoran were obtained in a yield of 17.0 g. The resultant compound exhibited a melting point of from 155° C. to 159° C.

A solution of the resultant compound in toluene was colorless and rapidly produced a black color when placed in contact with silica gel.

EXAMPLE 3

Preparation of
2-anilino-3-methyl-6-N,N-ditetrahydrofurfurylaminofluoran 2-(4-N,N-ditetrahydrofurfurylamino-2-hydroxybenzoyl)-benzoic acid in an amount of 19.1 g was completely dissolved in 150 g of a 100% sulfuric acid at a temperature of approximately 5° C. The solution was mixed with 11.5 g of 2-methyl-4-methoxydiphenylamine. The mixture was maintained at a temperature of 10° C. to 20° C. for 10 hours.

The resultant reaction mixture was treated in the same manner as that described in Example 1, and the resultant crystalline deposit was recrystallized from ethyl alcohol. White crystals consisting of 2-anilino-3-methyl-6-N,N-ditetrahydrofurfurylaminofluoran were obtained in a yield of 15.9 g. The resultant compound exhibited a melting point of from 174° C. to 176° C.

A solution of the resultant compound in toluene was colorless and rapidly produced a black color when placed in contact with silica gel.

EXAMPLE 4

Preparation of
2-(2-chlorophenyl)amino-6-N-methyl-N-tetrahydrofurfurylaminofluoran The same procedures as those described in Example 1 were carried out except that the 16.6 g of the 2-(4-N-ethyl-N-tetrahydrofurfurylamino-2-hydroxy-benzoyl)-benzoic acid were replaced by 16.0 g of 2-(4-N-methyl-N-tetrahydrofurfurylamino-2-hydroxy-benzoyl)-benzoic acid and the 11.5 g of the 2-methyl-4-methoxydiphenylamine were replaced by 12.6 g of 2'-chloro-4-methoxydiphenylamine.

Slightly pink white crystals consisting of 2-(2-chlorophenyl)amino-6-N-methyl-N-tetrahydrofurfurylaminofluoran were obtained in a yield of 17.7 g. The resultant compound exhibited a melting point of from 169° C. to 173° C.

A solution of the resultant compound in toluene was colorless and rapidly produced a black color when placed in contact with silica gel.

EXAMPLE 5

Preparation of
2-anilino-3-chloro-6-N-methyl-N-tetrahydrofurfurylaminofluoran

The same reaction procedures as those described in Example 1 were carried out except that 16.0 g of 2-(4-N-methyl-N-tetrahydrofurfurylamino-2-hydroxybenzoyl)benzoic acid were used as a benzophenone derivative and 12.6 g of 2-chloro-4-methoxydiphenylamine were used as a diphenyl amine derivative.

The resultant reaction mixture was treated in the same manner as that described in Example 1, and the resultant crystalline deposit was recrystallized from ethyl alcohol. White crystals consisting of 2-anilino-3-chloro-6-N-methyl-N-tetrahydrofurfurylaminofluoran were obtained in a yield of 14.5 g. The resultant compound exhibited a melting point of from 146° C. to 151° C.

A solution of the resultant compound in toluene was colorless and rapidly produced a greenish black color when placed in contact with silica gel.

EXAMPLE 6

Preparation of 2-(2-chlorophenyl)amino-6-N,N-ditetrahydrofurfurylaminofluoran

The same reaction procedures as those mentioned in Example 1 were carried out expect that 19.1 g of 2-(4-N,N,-ditetrahydrofurfurylamino-2-hydroxy-benzoyl)-benzoic acid were used as a benzophenone derivative and 12.6 g of 2'-chloro-4-methoxydiphenylamine were used as a diphenylamine derivative.

The resultant reaction mixture was treated in the same manner as that described in Example 1, and the resultant crystalline deposit was recrystallized from ethyl alcohol. White crystals consisting of 2-(2-chlorophenyl)amino-6-N,N-ditetrahydrofurfurylaminofluoran were obtained in a yield of 16.4 g. The resultant compound exhibited a melting point of from 164° C. to 166° C.

A solution of the resultant compound in toluene was colorless and rapidly produced a black color when placed in contact with silica gel.

EXAMPLE 7

Preparation of 2-anilino-3-methyl-6-N-n-butyl-N-tetrahydrofurfurylaminofluoran 2-(4-N-n-butyl-N-tetrahydrofurfurylamino-2-hydroxybenzoyl)-benzoic acid in an amount of 178 g was completely dissolved in 150 g of a 95% sulfuric acid at a temperature of approximately 5° C. The solution was mixed with 11.5 g of 2-methyl-4-methoxydiphenylamine. The mixture was maintained at a temperature of 5° to 10° C. for 10 hours.

The resultant reaction mixture was treated in the same manner as that described in Example 1, and the resultant crystalline deposit was recrystallized from ethyl alcohol. Slightly yellowish white crystals consisting of 2-anilino-3-methyl-6-N-n-butyl-N-tetrahydrofurfurylaminofluoran were obtained in an yield of 19.8 g. The resultant compound exhibited a melting point of from 155° C. to 158° C.

A solution of the resultant compound in toluene was colorless and rapidly produced a black color when placed in contact with silica gel.

EXAMPLE 8

Preparation of a heat-sensitive recording sheet. Three types of mixtures A, B, and C having the following compositions were milled for 3 hours by means of a paint conditioner.

| Component | Amount (parts by weight) |
|---|---|
| (A) | |
| 2-anilino-3-methyl-6-N—methyl-N—tetrahydrofurfurylaminofluoran | 4 |
| 10% polyvinyl alcohol aqueous solution | 34 |
| 5% defoaming agent solution*1 | 2 |
| (B) | |
| Bisphenol A | 6 |
| 10% polyvinyl alcohol aqueous solution | 20 |
| Water | 14 |
| (C) | |
| Aluminum hydroxide | 10 |
| 10% polyvinyl alcohol aqueous solution | 20 |
| Water | 10 |

Note: Defoaming agent - under the trademark of Sun Nopco 1407, made by Sun Nopco Co.

A coating liquid was prepared by mixing 3 parts by weight of the mixture A with 9 parts by weight of the mixture B, 5 parts by weight of the mixture C, and 3 parts by weight of water.

The coating liquid was coated on a surface of a high quality paper by means of a wire bar, and the coating liquid layer was dried in an air-blowing dryer at room temperature. The resultant recording layer had a dry weight of 5 g/m$^2$.

The color-forming sensitivity ($T_{1.0}$) and color fastness against humidity and oily substances of the resultant recording layer are shown in Table 2.

COMPARATIVE EXAMPLES 1 TO 3

The same procedures as those described in Example 8 were carried out except that the mixture A was replaced by the mixture D in Comparative Example 1, by the mixture E in Comparative Example 2, and by the mixture F in comparative Example 3, each mixture having the composition shown below.

| Component | Amount (parts by weight) |
|---|---|
| (D) | |
| 2-(2-chlorophenyl)amino-6-N,N—dibutylaminofluoran | 4 |
| 10% polyvinylalcohol aqueous solution | 34 |
| 5% defoaming agent solution | 2 |
| (E) | |
| 2-anilino-3-methyl-6-N—methyl-N—cyclohexyl aminofluoran | 4 |
| 10% polyvinyl alcohol aqueous solution | 34 |
| 5% defoaming agent aqueous solution | 2 |
| (F) | |
| 2-anilino-3-methyl-6-N—ethyl-N—isoamylaminofluoran | 4 |
| 10% polyvinyl alcohol aqueous solution | 34 |
| 5% defoaming agent aqueous solution | 2 |

The results are shown in Table 2.

EXAMPLES 9 TO 22

In each of Examples 9 to 22, the same procedures as those described in Example 8 were carried out except that the 2-anilino-3-methyl-6-N-methyl-N-tetrahydrofurfurylaminofluoran was replaced by the 6-tetrahydrofurfurylaminofluoran compound having the substituents $R_1$ $R_2$, and $R_3$ as shown in Table 2.

The results are shown in Table 2.

against humidity and oily substances. Therefore, the heat-sensitive recording sheet of the present invention is useful for various purposes, for example, high speed recording or label for point of sales (POS).

TABLE 2

| Example No. | Substituent $R_1$ | $R_2$ | $R_3$ | Color-forming sensitivity $T_{1.0}$ (°C.) | Color fastness against humidity | Color fastness against substances |
|---|---|---|---|---|---|---|
| Example | | | | | | |
| 8 | —CH$_3$ | —CH$_3$ | H | 107 | 108 | 85.6 |
| 9 | —C$_2$H$_5$ | —CH$_3$ | H | 110 | 97.9 | 95.8 |
| 10 | —CH$_2$—(tetrahydrofuryl) | —CH$_3$ | H | 115 | 106.0 | 82.6 |
| 11 | —CH$_3$ | H | 2-Cl | 125 | 77.7 | 35 |
| 12 | —CH$_3$ | —Cl | H | 127 | 65.0 | 34 |
| 13 | —CH$_2$—(tetrahydrofuryl) | —H | 2-Cl | 139 | 49.1 | 26 |
| 14 | —CH$_2$CH$_2$CH(CH$_3$)$_2$ | —CH$_3$ | H | 109 | 84.0 | 77.4 |
| 15 | —CH$_2$CH$_2$CH$_2$CH$_3$ | —CH$_3$ | H | 113 | 80.5 | 73.5 |
| 16 | —C$_6$H$_4$—CH$_3$ | —CH$_3$ | H | 127 | 63.1 | 40.0 |
| 17 | —C$_6$H$_{11}$ | —CH$_3$ | H | 110 | 83.2 | 62.1 |
| 18 | —CH$_3$ | —C$_2$H$_4$OC$_2$H$_5$ | H | 107 | 90.0 | 85.0 |
| 19 | —CH$_3$ | —C$_6$H$_5$ | H | 115 | 79.2 | 62.1 |
| 20 | —CH$_3$ | —CH$_2$—C$_6$H$_5$ | H | 120 | 66.2 | 38.5 |
| 21 | —CH$_3$ | —CH$_2$CH$_3$ | 4-CO—C$_6$H$_5$ | 109 | 67.0 | 45.1 |
| 22 | —CH$_3$ | —H | 2-F | 112 | 70.6 | 50.2 |
| Comparative Example | | | | | | |
| 1 | 2-(2-chlorophenyl)amino-6-N,N—dibutylaminofluoran | | | 139.5 | 27 | 11 |
| 2 | 2-anilino-3-methyl-6-N—methyl-N—cyclohexylaminofluoran | | | 126.5 | 60 | 20 |
| 3 | 2-anilino-3-methyl-6-N—ethyl-N—isoamylaminofluoran | | | 116.5 | 47 | 21 |

Table 2 clearly shows that the heat sensitive recording sheets containing the 6-tetrahydrofurfurylaminofluoran compound of the present invention exhibit an excellent heat-sensitivity and superior color fastness

EXAMPLE 23

The same procedures as those described in Example 8 were carried out except that in the mixture A, 4 parts by weight of the 2-anilino-3-methyl-6-N-methyl-N-tetrahydrofurfurylaminofluoran were replaced by a mixture of 2 parts by weight of 2-anilino-3-methyl-6-N-methyl-N-tetrahydrofurfurylaminofluoran with 2 parts by weight of 2-anilino-3-methyl-6-N-ethyl-N-tetrahydrofurfurylaminofluoran.

In the resultant recording sheet, the recording layer exhibited a $T_{1.0}$ of 119° C., a color fastness against humidity of 100 and a color fastness against oily substances of 92.8. Those properties are considered satisfactory.

We claim:

1. A 6-tetrahydrofurfurylaminofluoran compound of the formula (I):

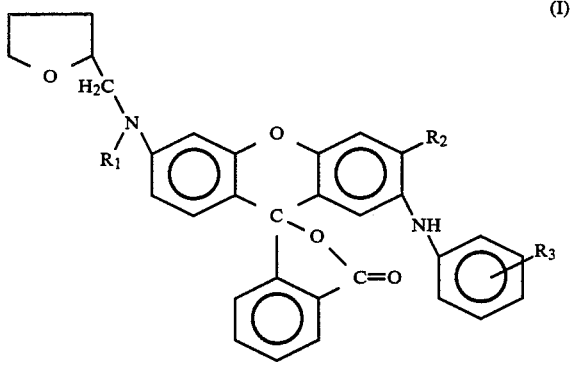

wherein $R_1$ represents a member selected from the group consisting of a hydrogen atom, alkyl radicals having 1 to 8 carbon atoms, a tetrahydrofurfuryl radical, a phenyl radical, an alkylphenyl radical in which the alkyl group has 1 to 5 carbon atoms, and cyclic alkyl radicals having 3 to 8 carbon atoms; $R_2$ represents a member selected from the group consisting of a hydrogen atom, chlorine atom, fluorine atom, alkyl radicals having 1 to 5 carbon atoms, alkoxy radicals having 1 to 5 carbon atoms, alkoxyalkyl radicals having 2 to 10 carbon atoms, a phenyl radical, and a benzyl radical; and $R_3$ represents a hydrogen atom, chlorine atom, fluorine atom, alkyl radicals having 1 to 5 carbon atoms, and acyl radicals having 2 to 7 carbon atoms.

2. The fluoran compound as claimed in claim 1, selected from 2-anilino-3-methyl-6-N-methyl-N-tetrahydrofurfurylaminofluoran, 2-anilino-3-methyl-6-N-ethyl-N-tetrahydrofurfurylaminofluoran, 2-anilino-3-chloro-6-N-methyl-N-tetrahydrofurfurylaminofluoran, 2-(2-chloroanilino)-6-N-methyl-N-tetrahydrofurfurylaminofluoran, 2-(2-chloroanilino)-6-N,N-ditetrahydrofurfurylaminofluoran, 2-anilino-3-methyl-6-N,N-ditetrahydrofurfurylaminofluoran, 2-anilino-3-methyl-6-N-isoamyl-N-tetrahydrofurfurylaminofluoran, 2-anilino-3-methyl-6-N-butyl-N-tetrahydrofurfurylaminofluoran, 2-anilino-3-ethoxyethyl-6-N-methyl-N-tetrahydrofurfurylaminofluoran, 2-anilino-3-methyl-N-p-tolyl-N-tetrahydrofurfurylaminofluoran, 2-anilino-3-methyl-6-N-cyclohexyl-N-tetrahydrofurfurylaminofluoran, 2-anilino-3-methyl-N-tetrahydrofurfurylaminofluoran, 2-anilino-3-phenyl-6-N-methyl-N-tetrahydrofurfurylaminofluoran, 2-anilino-3-phenyl-6-N-ethyl-N-tetrahydrofurfurylaminofluoran, 2-anilino-3-benzyl-6-N-methyl-N-tetrahydrofurfurylaminofluoran, 2-anilino-3-methoxy-6-N-methyl-N-tetrahydrofurfurylaminofluoran, 2-p-toluidino-3-methyl-6-N-methyl-N-tetrahydrofurfurylaminofluoran, 2-(p-benzoyl-phenylamino)-3-ethyl-6-N-methyl-N-tetrahydrofurfurylaminofluoran, 2-(2-fluoroanilino)-6-N-methyl-N-tetrahydrofurfurylaminofluoran, and 2-anilino-3-benzyl-6-N,N-ditetrahydrofurfurylaminofluoran.

3. A heat-sensitive color-former comprising at least one 6-tetrahydrofurfurylaminofluoran compound as claimed in claim 1.

* * * * *

UNITED STATES PATENT AND TRADEMARK OFFICE
CERTIFICATE OF CORRECTION

PATENT NO. : 4,597,795
DATED : July 1, 1986
INVENTOR(S) : Hideyuki Sensui et al.

It is certified that error appears in the above—identified patent and that said Letters Patent is hereby corrected as shown below:

Column 6, line 12, "hydrocarbons" should be --hydrocarbon--.

Column 7, line 33, "1 1" should be --1 $\ell$--

Column 9, line 21, "expect" should be --except--.

Signed and Sealed this

Twenty-eighth Day of October, 1986

[SEAL]

Attest:

DONALD J. QUIGG

*Attesting Officer*   *Commissioner of Patents and Trademarks*